(12) United States Patent
Su

(10) Patent No.: US 8,921,390 B2
(45) Date of Patent: Dec. 30, 2014

(54) MEDICAMENTS FOR INHIBITING THROMBUS FORMATION

(75) Inventor: Chunhua Su, Guangzhou (CN)

(73) Assignee: Guizhou Liansheng Pharmaceutical Co. Ltd., Zunyi, Guizhou Province (CN)

( * ) Notice: Subject to any disclaimer, the term of this patent is extended or adjusted under 35 U.S.C. 154(b) by 2 days.

(21) Appl. No.: 13/496,290

(22) PCT Filed: Mar. 17, 2010

(86) PCT No.: PCT/CN2010/000328
§ 371 (c)(1),
(2), (4) Date: Mar. 15, 2012

(87) PCT Pub. No.: WO2011/044742
PCT Pub. Date: Apr. 21, 2011

(65) Prior Publication Data
US 2012/0178777 A1    Jul. 12, 2012

(30) Foreign Application Priority Data

Oct. 15, 2009  (CN) .......................... 2009 1 0193077

(51) Int. Cl.
| | | |
|---|---|---|
| *A61K 31/44* | (2006.01) | |
| *A01N 37/36* | (2006.01) | |
| *A61K 31/4365* | (2006.01) | |
| *A61K 9/20* | (2006.01) | |
| *A61K 9/48* | (2006.01) | |
| *A61K 31/616* | (2006.01) | |
| *A61K 45/06* | (2006.01) | |

(52) U.S. Cl.
CPC ........... *A61K 31/4365* (2013.01); *A61K 9/2018* (2013.01); *A61K 9/2027* (2013.01); *A61K 9/2054* (2013.01); *A61K 9/2059* (2013.01); *A61K 9/4866* (2013.01); *A61K 31/616* (2013.01); *A61K 45/06* (2013.01)
USPC ........... 514/301; 514/159; 514/163; 514/277; 514/279; 514/299

(58) Field of Classification Search
USPC .......... 560/129, 130; 514/159, 163, 277, 279, 514/299, 301
See application file for complete search history.

(56) References Cited

U.S. PATENT DOCUMENTS

| | | | | |
|---|---|---|---|---|
| 3,019,253 | A * | 1/1962 | Hauptschein | 560/130 |
| 4,096,252 | A * | 6/1978 | Barra et al. | 514/159 |
| 5,576,328 | A * | 11/1996 | Herbert et al. | 514/301 |
| 6,635,763 | B2 * | 10/2003 | Pandey et al. | 546/114 |
| 6,737,411 | B2 * | 5/2004 | Valeriano et al. | 514/39 |
| 2010/0069326 | A1 * | 3/2010 | Haque et al. | 514/56 |

FOREIGN PATENT DOCUMENTS

| | | | | |
|---|---|---|---|---|
| WO | WO2008048083 A1 * | 4/2008 | ......... | A61K 31/4365 |
| WO | WO2009100534 A1 * | 8/2009 | ........... | A61K 31/235 |

* cited by examiner

*Primary Examiner* — My-Chau T Tran
(74) *Attorney, Agent, or Firm* — Novoclaims Patent Services LLC; Mei Lin Wong

(57) ABSTRACT

A Medicaments for inhibiting thrombus formation contains active ingredients which are triflusal and clopidogrel bisulfate, wherein a mass ratio of triflusal to clopidogrel bisulfate is (100-650):(30-150), preferably (1-20):1, more preferably (3-6):1, and even more preferably 3:1 or 6:1.

20 Claims, 2 Drawing Sheets

MEDICAMENTS FOR INHIBITING THROMBUS FORMATION

BACKGROUND OF THE PRESENT INVENTION

1. Field of Invention

The present invention relates to medicaments for inhibiting thrombus formation.

2. Description of Related Arts

An incidence, morbidity, and mortality of thrombotic diseases such as myocardial infarction and cerebral thrombus formation are among the toppest in a variety of diseases. Stenosis and thrombus formation of Coronary artery or cerebrovascular artery are formed on a basis of atherosclerosis and caused by repeat injury of blood vessels. When the blood vessels are suffered from injury, platelets, which are adhered to to exposed subcutaneous tissue, release contents in the particles thereof which are adenosine diphosphate (ADP), and thromboxane $A_2$ ($TXA_2$) formed from metabolism of membrane phospholipid. These two contents activate platelets which are in the circulation, and the activated platelets are then aggregated to form platelets thrombosis with an existence of fibrinogen. The injury of blood vessels also activates the coagulation system, and the generated thrombin promotes a further aggregation of the platelets and fibrin is subsequently formed, so that stability of arterial thrombus is enhanced after crosslinking with fibrin. Anti-platelet drugs inhibit thrombus formation by inhibiting adhesion, aggregation, and release of the plates, and thus play an important role in prevention and treatment of thrombotic diseases.

Triflusal is a kind of agent for preventing aggregation of platelets and has an extraordinary effect in prevention and treatment of thrombotic diseases and complicating diseases in comparison with acetylsalicylic acid (aspirin), for triflusal is capable of antagonizing activity of cyclooxygenase and c-AMP phosphodiesterase at the same time and has an effective effect for inhibiting aggregation of platelets. In the meantime, triflusal, which is in therapeutic doses, has little influence on biosynthesis of prostacyclin and the risk of bleeding is also a minimum. Studies have shown that there is no difference when triflusal and aspirin are employed to prevent severe cardiovascular events for patients with peripheral arterial occlusive disease (PAOD), but the incidence of complicating diseases when using triflusal is much less than using aspirin.

Clopidogrel is commonly used for inhibiting aggregation of platelets. The mechanism is that P2Y12 which is ADP receptor takes irreversible changes and selectively inhibits aggregation of platelets induced by ADP, and aggregation induced by collagen and thrombin are also can be inhibited. It is now widely accepted that in comparison with aspirin, clopidogrel is more effective. But it is believed that clopidogrel does not have advantages in other benefits for the authorities have not yet submitted a prove that clopidogrel plays better than aspirin. For those who have a contraindication to low-dose aspirin, clopidogrel (75 mg/d) is a good alternative drug for patients with high risk coronary cerebrovascular disease or peripheral vascular diseases.

SUMMARY OF THE PRESENT INVENTION

A main object of the present invention is to provide medicaments for inhibiting thrombus formation.

Additional advantages and features of the invention will become apparent from the description which follows, and may be realized by means of the instrumentalities and combinations particular point out in the appended claims.

According to the present invention, the foregoing and other objects and advantages are attained by medicaments containing active ingredients which are triflusal and clopidogrel bisulfate, wherein a mass ratio of triflusal to clopidogrel bisulfate is (100-650):(30-150).

In the active ingredients of the medicaments, the mass ratio of triflusal to clopidogrel bisulfate can be (100-600):(30-100), preferably (100-600):(50-100).

In the active ingredients of the medicaments, the mass ratio of triflusal to clopidogrel bisulfate can be (100-600):(92-104), preferably (300-600):(92-104).

In the active ingredients of the medicaments, the mass ratio of triflusal to clopidogrel bisulfate can be (250-650):(50-150).

Preferably, the mass ratio of triflusal to clopidogrel bisulfate is (285-315):(95-105).

Preferably, the mass ratio of triflusal to clopidogrel bisulfate is (570-630):(95-105).

In the active ingredients of the medicaments, the mass ratio of triflusal to clopidogrel bisulfate can be (1-20):1, preferably (3-6):1, and more preferably 3:1 or 6:1.

In the active ingredients of the medicaments, the mass ratio of triflusal to clopidogrel bisulfate can be (300-600):98±5%, preferably 300:97.875 or 600:97.875.

The above medicaments, which are in a unit therapeutic dose, may contain 130-800 mg active ingredients, preferably 130-700 mg.

The above medicaments, which are in a unit therapeutic dose, may contain 100-600 mg triflusal and 30-100 mg clopidogrel bisulfate, preferably 100-600 mg triflusal and 50-100 mg clopidogrel bisulfate.

The above medicaments, which are in a unit therapeutic dose, may contain 100-600 mg triflusal and 92-104 mg clopidogrel bisulfate, preferably 300-600 mg triflusal and 92-104 mg clopidogrel bisulfate.

The above medicaments, which are in a unit therapeutic dose, may contain 285-315 mg triflusal and 95-105 mg clopidogrel bisulfate, preferably 300 mg triflusal and 100 mg clopidogrel bisulfate.

The above medicaments, which are in a unit therapeutic dose, may contain 570-630 mg triflusal and 95-105 mg clopidogrel bisulfate, preferably 600 mg triflusal and 100 mg clopidogrel bisulfate The medicaments can be prepared for oral use.

The medicaments can be prepared as tablets, capsules, granules, or dry suspension.

The medicaments may contain at least one of accessories which is selected from the group consisting of microcrystalline cellulose, sodium carboxymethyl starch, dextrin, lactose, and magnesium stearate.

The medicaments are used in the treatment of cardiovascular and cerebrovascular diseases which may be caused by aggregation of platelets. The cardiovascular and cerebrovascular diseases are at least one of diseases selected form the group consisting of angina, coronary thrombus formation, and cerebral embolism.

The medicaments can be used to inhibit platelet aggregation and/or thrombus formation.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
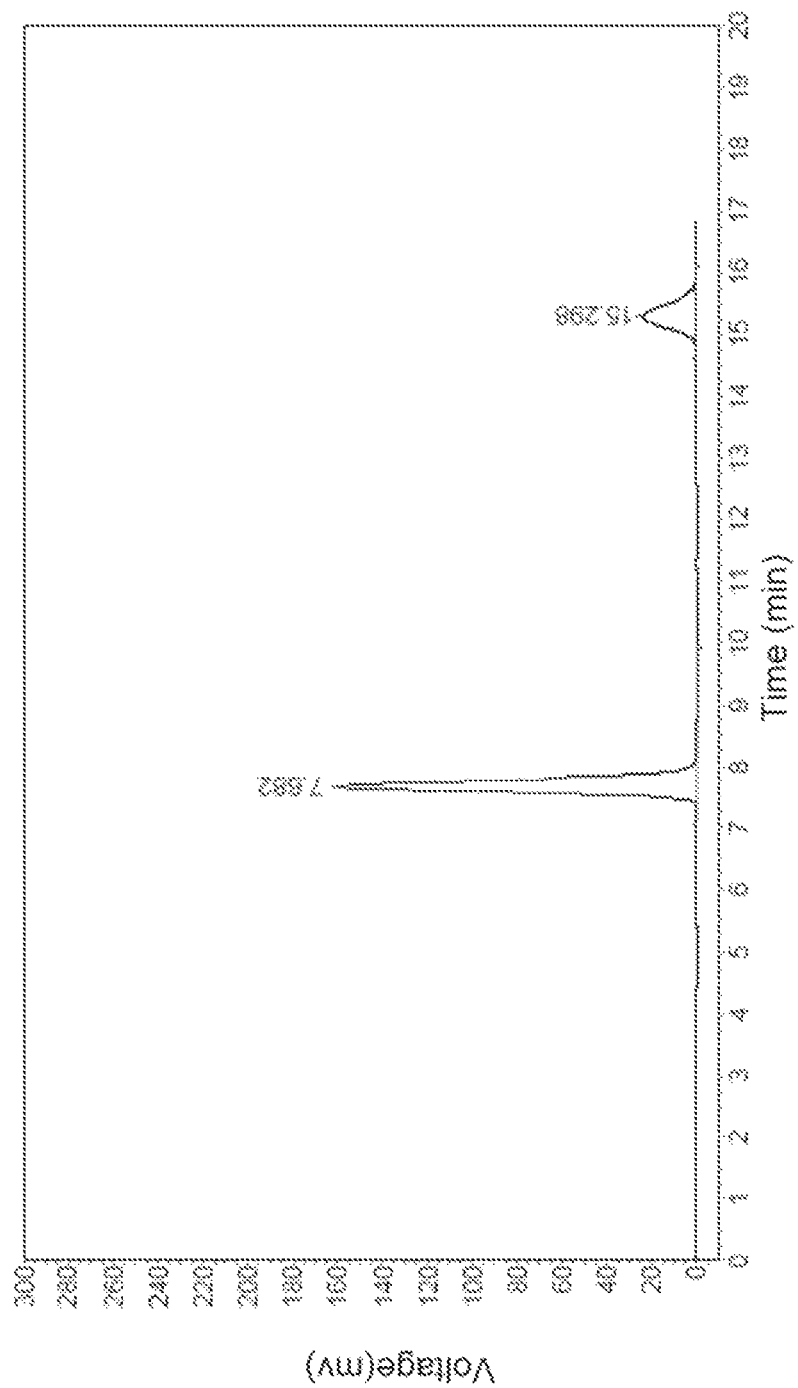
FIG. 1 is a spectrum diagram of specimen II.

The following description is disclosed to enable any person skilled in the art to make and use the present invention. Preferable embodiments are provided in the following description only as examples and modifications will be apparent to those skilled in the art. The general principles defined in the following description would be applied to other embodiments, alternatives, modifications, equivalents, and applications without departing from the spirit and scope of the present invention.

In the following disclosure, the experiment methods in the following embodiment are conventional methods unless specially identified. The materials can be obtained from a common biochemical reagent shop unless specially identified. The symbol "%" is used for a mass ratio percentage unless specially identified.

Triflusal, clopidogrel, and clopidogrel bisulfate are purchased from the development center of Dalian Tianyu Haibin Pharmaceutial Co., Ltd.

Embodiment 1:performance of Inhibiting Thrombus Formation and Platelet Aggregation of the Medicaments of the Present Invention Firstly, performance of inhibiting thrombus formation on albino rat is disclosed hereafter.

130 SD albino rats, in which 65 male rats and 65 female rats, with weight of 300-400 g were employed to do the experiments. All of the 130 rats were divided into thirteen groups each having ten rats. The administration was carried out as follows: Group 1 is a control group in which physiological saline was administered; Group 2 is another control group in which compound drugs which were triflusal and clopidogrel were administered, wherein a mass ratio of triflusal to clopidogrel was 1:1; Group 3: administering medicaments of the present invention in which a mass ratio of triflusal to clopidogrel bisulfate was 20:1; Group 4: administering medicaments of the present invention in which the mass ratio of triflusal to clopidogrel bisulfate was 12:1; Group 5: administering medicaments of the present invention in which the mass ratio of triflusal to clopidogrel bisulfate was 6:1; Group 6: administering medicaments of the present invention in which the mass ratio of triflusal to clopidogrel bisulfate was 3:1; Group 7: administering medicaments of the present invention in which the mass ratio of triflusal to clopidogrel bisulfate was 1:1; Group 8: administering only triflusal; Group 9: administering only clopidogrel bisulfate; Group 10: administering drugs in which the mass ratio of triflusal to clopidogrel was 20:1; Group 11: administering drugs in which the mass ratio of triflusal to clopidogrel was 12:1; Group 12: administering drugs in which the mass ratio of triflusal to clopidogrel was 6:1; Group 13: administering drugs in which the mass ratio of triflusal to clopidogrel was 3:1.

Method of the experiments: intragastric administration for each group, wherein the control group 1 was administered with physiological saline of a same mass and other groups were administered with drugs as described above. The administration was carried out for five days and one time a day, wherein the dose of the administration was 10 mg drugs/kg body weight of the rat (For compound drugs, the total mass of all of the ingredients was 10 mg).

At one hour after the last administration on the fifth day of the administration period, the weight of the rat was measured, and 3% pelltobarbitalum natricum with a dose of 1 ml/kg body weight was injected for anesthesia. The rat was lying in a supine position and was cut at the middle of the neck, wherein the trachea was separated, and the carotid and jugular vein were also separated. A 6 cm silk thread penetrated through a polyethylene pipe which was then filled with heparin saline solution. When a first end of the polyethylene pipe was embedded into the jugular vein on the left side, heparin was injected into the jugular vein for anti-aggregation. And then a second end of the polyethylene pipe was embedded into the carotid on the right side. The bulldog camp was opened and an A-V bypass was formed. Keep bleeding for 15 mins, and then the polyethylene pipe was taken out and the silk thread (containing thrombus) was also pulled out. The silk thread (containing thrombus) was collected in order and put in a small petri dish which has a known weight. A wet weight was measured with an analytical balance. The total wet weight minus the weight of the silk thread so that the weight of the thrombus was obtained. A thrombus formation inhibiting rate (%)=(weight of the thrombus in the control group in which physiological saline was administered−weight of the thrombus in the experimental group in which drugs or medicaments of the present invention was administered)/weight of the thrombus in the control group in which physiological saline was administered×100%.

TABLE 1

A comparison of weights of the thrombus-of the experimental groups($\chi \pm s$).

| Group number | Dose (mg/kg) | NO. of rats | Wet weight (mg) | Inhibiting rate |
|---|---|---|---|---|
| 1 |    | 10 | 44.22 ± 0.52 |    |
| 2 | 10 | 10 | 21.20 ± 0.40** | 52.06%** |
| 3 | 10 | 10 | 18.21 ± 0.34** | 58.81%** |
| 4 | 10 | 10 | 16.20 ± 0.41** | 63.36%** |
| 5 | 10 | 10 | 13.35 ± 0.50** | 69.81%** |
| 6 | 10 | 10 | 13.44 ± 0.21** | 69.61%** |
| 7 | 10 | 10 | 17.22 ± 0.32** | 61.05%** |
| 8 | 10 | 10 | 22.25 ± 0.44** | 49.68%** |
| 9 | 10 | 10 | 24.31 ± 0.30** | 45.02%** |
| 10 | 10 | 10 | 20.89 ± 0.45** | 52.76%** |
| 11 | 10 | 10 | 20.01 ± 0.36** | 54.75%** |

TABLE 1-continued

A comparison of weights of the thrombus-of
the experimental groups($\chi \pm s$).

| Group number | Dose (mg/kg) | NO. of rats | Wet weight (mg) | Inhibiting rate |
|---|---|---|---|---|
| 12 | 10 | 10 | 19.33 ± 0.45** | 56.29%** |
| 13 | 10 | 10 | 20.50 ± 0.51** | 53.64%** |

It should be noticed that the control group in which physiological saline was administered was taken for comparison, and **P was less than 0.01.

It can be concluded that triflusal, clopidogrel, and clopidogrel bisulfate can cooperate with other when combine to inhibit thrombus formation. And at a same ratio 1:1, the performance of the group 7 in which triflusal and clopidogrel bisulfate were administered was better than the group 2 in which triflusal and clopidogrel were administered. At other same ratios, the performance of the groups in which triflusal and clopidogrel bisulfate were administered were also better than the groups in which triflusal and clopidogrel were administered. A preferable ratio of triflusal to clopidogrel was 6:1 or 3:1. The performance of the groups in which triflusal and clopidogrel bisulfate were administered was better than the groups in which only triflusal or only clopidogrel bisulfate was used.

Secondly, performance of inhibiting platelet aggregation on albino rat is described in the following disclosure (method of nephelometery).

130 SD albino rats, in which 65 male rats and 65 female rats, with weight of 300-400 g were employed to do the experiments. All of the 130 rats were divided into thirteen groups each having ten rats. The administration was carried out as follows: Group 1 is a control group in which physiological saline was administered; Group 2 is another control group in which compound drugs which were triflusal and clopidogrel were administered, wherein a mass ratio of triflusal to clopidogrel was 1:1; Group 3: administering medicaments of the present invention in which a mass ratio of triflusal to clopidogrel bisulfate was 20:1; Group 4: administering medicaments of the present invention in which the mass ratio of triflusal to clopidogrel bisulfate was 12:1; Group 5: administering medicaments of the present invention in which the mass ratio of triflusal to clopidogrel bisulfate was 6:1; Group 6: administering medicaments of the present invention in which the mass ratio of triflusal to clopidogrel bisulfate was 3:1; Group 7: administering medicaments of the present invention in which the mass ratio of triflusal to clopidogrel bisulfate was 1:1; Group 8: administering only triflusal; Group 9: administering only clopidogrel bisulfate; Group 10: administering drugs in which the mass ratio of triflusal to clopidogrel was 20:1; Group 11: administering drugs in which the mass ratio of triflusal to clopidogrel was 12:1; Group 12: administering drugs in which the mass ratio of triflusal to clopidogrel was 6:1; Group 13: administering drugs in which the mass ratio of triflusal to clopidogrel was 3:1.

Method of the experiments: intragastric administration for each group, wherein the control group 1 was administered with physiological saline of a same mass and other groups were administered with drugs as described above. The administration was carried out for seven days and one time a day, wherein the dose of the administration was 10 mg drugs/kg body weight of the rat (For compound drugs, the total mass of all of the ingredients was 10 mg).

At half an hour after the last administration on the seventh day of the administration period, blood sample was obtained from artery behind eyes of the rat. 0.13% sodium citrate was added thereto as an anticoagulant. The blood was injected into a silicon tube and a plastic film was used to cover the mouth of the silicon tube. Upsetting the silicon tube 3-4 times to evenly mix the blood and the anticoagulant. The residual blood adhered on the inner surface of the silicon tube was removed by clean filter paper, and then the mouth of the tube was sealedly closed. The tube was centrifuged for 10 min at a speed of 1000 r/min, the blood plasma on the top was carefully taken out and the rest blood plasma was centrifuged for 20 min at a speed of 2000 r/min, and finally the transparent solution in the bottom was PPP. The number of the platelets in the PRP was calculated and was adjusted to $200 \times 10^9$/L using PPP. 450 μl PPP and PRP were obtained by pietes which has been siliconized and added into an opacity tube respectively. Before measuring, the transmittancy of the grapher recording meter was adjusted to 100 using PPP specimen. A PRP specimen was then put into the measuring chamber and the transmittancey was then adjusted to 10. A stirring bar magnet was added, and preheated for 3 min at 37° C. Open the grapher recording meter, add ADP (adenosine diphosphate) which was inducing agent for platelet aggregation into PRP. Use a CHROND-Log platelet aggregation meter to calculate the maximum platelet aggregation rate (%) through an aggregation curve, wherein Amax=h1/h0×100%. The platelet aggregation inhibiting rate=[(Amax of physiological saline group−Amax of to experimental group with administering drug)/Amax of physiological saline group]×100%. The results were shown in Table 2.

TABLE 2

Influence on platelet aggregation of the
experimental groups ($\chi \pm s$).

| Group number | Dose (mg/kg) | No. of rats | Amax (%) | inhibiting rate (%) |
|---|---|---|---|---|
| 1 | 10 | 10 | 67.32 ± 3.52 | |
| 2 | 10 | 10 | 35.20 ± 3.40** | 47.71** |
| 3 | 10 | 10 | 33.21 ± 3.34** | 50.67** |
| 4 | 10 | 10 | 29.20 ± 1.41** | 56.62** |
| 5 | 10 | 10 | 25.57 ± 3.27** | 62.02** |
| 6 | 10 | 10 | 27.29 ± 2.72** | 59.46** |
| 7 | 10 | 10 | 31.22 ± 1.32** | 53.62** |
| 8 | 10 | 10 | 38.25 ± 2.44** | 43.18** |
| 9 | 10 | 10 | 40.31 ± 2.30** | 40.12** |
| 11 | 10 | 10 | 37.55 ± 2.40** | 44.22** |
| 11 | 10 | 10 | 36.88 ± 3.44** | 45.21** |
| 12 | 10 | 10 | 36.10 ± 3.67** | 46.38** |
| 13 | 10 | 10 | 36.50 ± 3.20** | 45.78** |

It also should be noticed that the control group in which physiological saline was administered was taken for comparison, and **P was less than 0.01.

The results suggested that the performance of the groups in which triflusal and clopidogrel bisulfate were administered was better than the groups in which only triflusal or only clopidogrel was used. At same ratios, the performance of the groups in which triflusal and clopidogrel bisulfate were administered were better than the groups in which triflusal and clopidogrel were administered.

Thirdly, the stability of the medicaments of the present invention was also studied.

The experimental specimens are prepared with mass ratios as follows.

Specimen I: the mass ratio of trifusal to clopidogrel bisulfate was 1:1.

Specimen II: the mass ratio of trifusal to clopidogrel bisulfate was 3:1.

Specimen III: the mass ratio of trifusal to clopidogrel bisulfate was 6:1.

Specimen IV: the mass ratio of trifusal to clopidogrel bisulfate was 12:1.

Specimen V: the mass ratio of trifusal to clopidogrel bisulfate was 20:1.

Control specimen I: the mass ratio of trifusal to clopidogrel was 1:1.

Control specimen II: the mass ratio of trifusal to clopidogrel bisulfate was 3:1.

Control specimen III: the mass ratio of trifusal to clopidogrel bisulfate was 6:1.

Control specimen IV: the mass ratio of trifusal to clopidogrel bisulfate was 12:1.

Control specimen V: the mass ratio of trifusal to clopidogrel bisulfate was 20:1.

Figure 2:
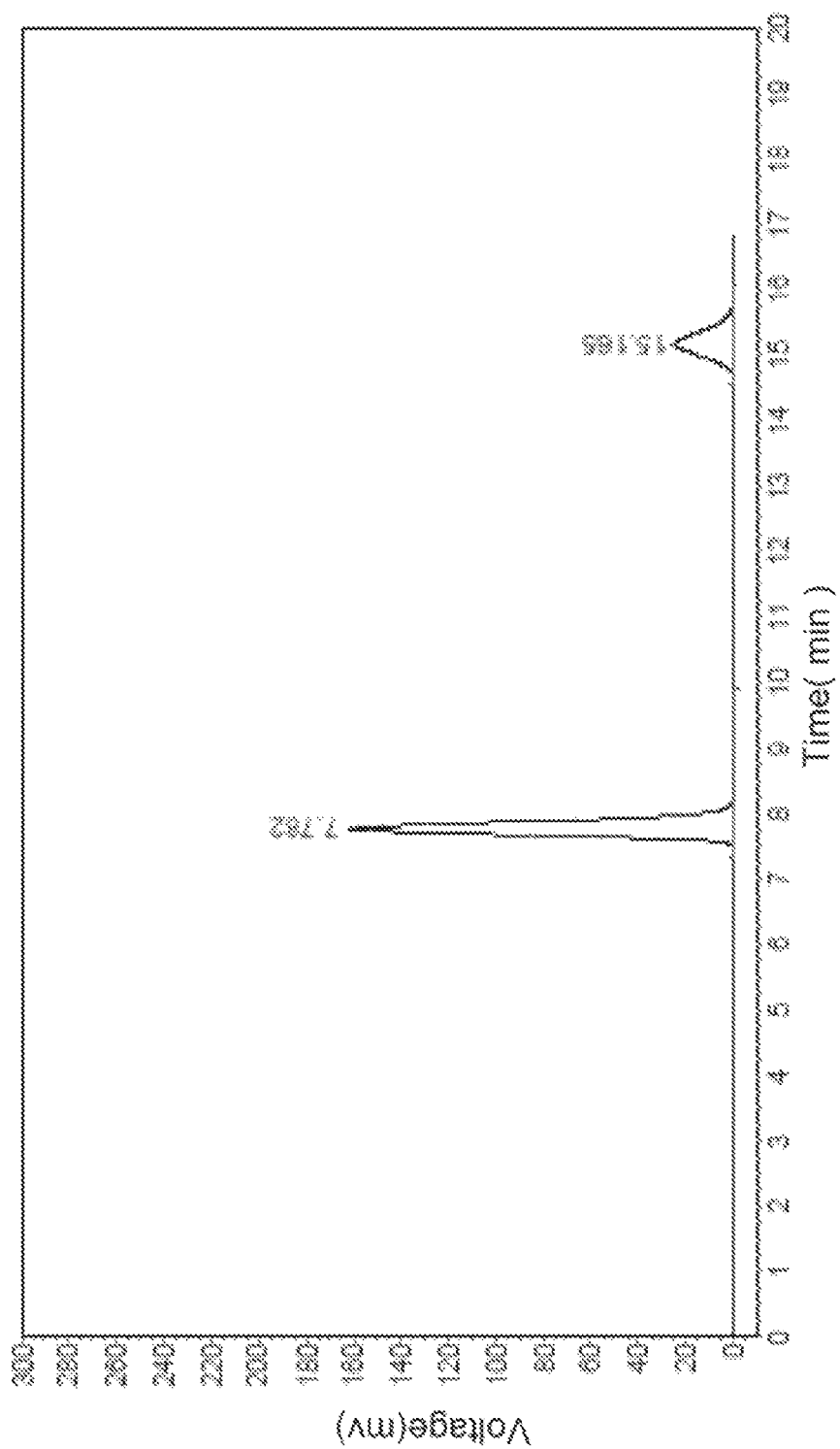
FIG. 2 is a spectrum diagram of control specimen II.

10 g samples of the above specimens were put in a medical plastic container and kept for six months at a temperature of 40° C.±2° C. and a moisture capacity of 75%±5%. The outer appearance and effective ingredient mass were observed in 0, 1st, 3rd, and 6th month. The effective ingredient was measured using High Performance Liquid Chromatography, wherein the column was a cyano column, the mobile phase was methanel-water-triethylamine (volume ratio of 500:500:2, pH was adjusted to 3.8 using phosphoric acid), flow rate was 1 ml/min, the detection wavelength was 235 nm, the column temperature was 35° C., the injection volume was 20 μl. Under the above condition, clopidogrel bisulfate with triflusal, and clopidogrel with triflusal were both can be completely separated and have a good separating size. The mass concentration of clopidogrel bisulfate at 12.0~100.0 mg/l had a good linear relation with peak area, wherein a regression equation $A=0.176C+0.0474 r=0.9995$; The mass concentration of clopidogrel at 9.2~75.9 mg/l had a good linear relation with peak area, wherein a regression equation $A=0.191C+0.0584 r=0.9997$; The mass concentration of triflusal at 38.4~320.0 mg/l had a good linear relation with peak area, wherein a regression equation $A=0.2991C+0.9882 r=0.9997$. An even yield rate of clopidogrel bisulfate, clopidogrel, and triflusal was 99.7±1.80%, 99.2±1.01%, 100.2±0.81% respectively, so that HPLC was suitable to be employed for measurement of clopidogrel bisulfate, clopidogrel, and triflusal. The retention time of clopidogrel bisulfate, clopidogrel, and triflusal was 15.298 min, 15.65 min, and 7.682 min respectively. The spectrum diagram of the specimen II was shown in FIG. 1, and the spectrum diagram of the control specimen II was shown in FIG. 2. The results were shown in table 3 and table 4.

TABLE 3

Residual mass of clopidogrel bisulfate and triflusal in the medicaments on different depositing time(In the following table, A: triflusal; B: clopidogrel bisulfate; C: clopidogrel).

| Time | Specimen I | | Specimen II | | Specimen III | | Specimen IV | | Specimen V | |
|---|---|---|---|---|---|---|---|---|---|---|
| (month) | A | B | A | B | A | B | A | B | A | B |
| 0 | 5 g | 5 g | 7.50 g | 2.50 g | 8.57 g | 1.43 g | 9.20 g | 0.80 g | 9.52 g | 0.48 g |
| 1 | 5.03 g | 4.96 g | 7.47 g | 2.50 g | 8.55 g | 1.42 g | 9.19 g | 0.81 g | 9.55 g | 0.47 g |
| 2 | 5.04 g | 5.03 g | 7.46 g | 2.48 g | 8.54 g | 1.41 g | 9.13 g | 0.80 g | 9.0 g | 0.46 g |
| 3 | 4.98 g | 5.08 g | 7.40 g | 2.48 g | 8.56 g | 1.44 g | 9.21 g | 0.82 g | 9.49 g | 0.48 g |
| 6 | 4.99 g | 4.97 g | 7.52 g | 2.49 g | 8.62 g | 1.43 g | 9.14 g | 0.80 g | 9.5 mg | 0.49 g |

TABLE 4

Residual mass of clopidogrel and triflusal in the medicaments on different depositing time(In the following table, A: triflusal; B: clopidogrel bisulfate; C: clopidogrel).

| Time | Control specimen I | | Control specimen II | | Control specimen III | | Control specimen IV | | Control specimen V | |
|---|---|---|---|---|---|---|---|---|---|---|
| (month) | A | C | A | C | A | C | A | C | A | C |
| 0 | 5 g | 5 g | 7.50 g | 2.50 g | 8.57 g | 1.43 g | 9.20 g | 0.80 g | 9.52 g | 0.48 g |
| 1 | 5.01 g | 4.96 g | 7.42 g | 2.47 g | 8.56 g | 1.40 g | 9.19 g | 0.78 g | 9.52 g | 0.47 g |
| 2 | 5.02 g | 4.83 g | 7.55 g | 2.43 g | 8.57 g | 1.38 g | 9.18 g | 0.73 g | 9.51 g | 0.47 g |
| 3 | 4.98 g | 4.79 g | 7.40 g | 2.41 g | 8.58 g | 1.32 g | 9.19 g | 0.72 g | 9.48 g | 0.45 g |
| 6 | 4.98 g | 4.66 g | 7.48 g | 2.32 g | 8.54 g | 1.25 g | 9.20 g | 0.69 g | 9.46 g | 0.41 g |

The results has shown that at each mass ratio, stability of the compound drug of triflusal and clopidogrel bisulfate was better than the compound drug of triflusal and clopidogrel at room temperature.

Embodiment 2: preparing and Application of Drugs (Capsule) for Curing Cardiovascular and Cerebrovascular Diseases (1) Preparing Capsule of Triflusal and Clopidogrel Bisulfate.

100 g triflusal and 30 g clopidogrel bisulfate were evenly mixed, 2 g magnesium stearate was added thereto and evenly mixed, 1000 capsules were then filled and prepared with the mixture.

(2) Preparing Capsule of Triflusal and Clopidogrel Bisulfate.

600 g triflusal and 100 g clopidogrel were evenly mixed, suitable amount of dextrin was added thereto and evenly mixed, 1000 capsules were then filled and prepared with the mixture.

(3) Preparing Capsule of Triflusal and Clopidogrel.

300 g triflusal and 75 g clopidogrel were evenly mixed, 120 g carboxymethyl starch and 5 g magnesium stearate were added thereto and evenly mixed, 1000 capsules were then filled and prepared with the mixture.

(4) Preparing Capsule of Triflusal and Clopidogrel 600 g triflusal and 75 g clopidogrel were evenly mixed, suitable amount of dextrin was added thereto and evenly mixed, 1000 capsules were then filled and prepared with the mixture.

(5) Preparing of Capsule of Compound Drug of Triflusal and Clopidogrel Bisulfate.

300 g triflusal, 97.875 g clopidogrel bisulfate, 100 g carboxymethyl starch, and 2.1 g magnesium stearate were evenly mixed, 1000 capsules were then filled and prepared with the mixture.

Embodiment 3: preparing of Drugs (Tablet) for Curing Cardiovascular and Cerebrovascular Diseases (1) Preparing Tablet Containing 600 mg Triflusal and 97.9 mg Clopidogrel Bisulfate.

97.9 mg clopidogrel bisulafate and 2 mg anhydrous colloidal silicon dioxide were mixed, 30 mg cornstarch which was pre-gelatinated and 20 mg anhydrous lactose were added thereto and evenly mixed, and then 600 mg triflusal and 30 mg microcrystalline cellulose were added thereto and underwent a tabletting process to prepare the final tablet product.

(2) Preparing Tablet of Compound Drug of Triflusal and Clopidogrel Bisulfate.

300 g triflusal and 97.875 g clopidogrel bisulfate were evenly mixed, 150 g microcrystalline cellulose and 10 g cross-linked polyvinylpyrrolidone were added thereto, the resulting mixture was grinded and soften by ethanol. Screening by 60 mesh sieve for preparing granules and dry at 50° C. Screening by 60 mesh sieve. 10 g carboxymethyl starch sodium, 2 g aspartame, and 30 g magnesium stearate were added thereto and evenly mixed. 1000 tables were finally prepared after a tabletting process.

(3) Preparing Tablet of Compound Drug of Triflusal and Clopidogrel Bisulfate.

600 g triflusal, 97.875 g clopidogrel bisulfate, suitable amount of starch and a small amount of magnesium stearate were evenly mixed. The mixture directly underwent a tabletting process to prepare 1000 tablets.

INDUSTRIAL APPLICATION

The present invention provides medicaments for curing cardiovascular and cerebrovascular diseases. The active ingredient in the medicaments are triflusal and clopidogrel bisulfate which cooperate during application. The results of the experiments have shown that the performance on inhibiting thrombus formation and platelet aggregation of triflusal and clopidogrel bisulfate was much better than triflusal and clopidogrel (control), and also the performance was much better than just using triflusal or clopidogrel bisulfate. According to a six-month observation, stability of the compound drug of triflusal and clopidogrel bisulfate was better than the compound drug of triflusal and clopidogrel.

What is claimed is:

1. A Medicaments for inhibiting thrombus formation, containing active ingredients which are triflusal and clopidogrel bisulfate, wherein a mass ratio of triflusal to clopidogrel bisulfate is (100-650):(30-150), wherein the medicaments is formulated in a single medication.

2. The medicaments as recited in claim 1, wherein in said active ingredients of said medicaments, said mass ratio of triflusal to clopidogrel bisulfate is (100-600):(92-104), preferably (300-600):(92-104).

3. The medicaments as recited in claim 1, wherein in said active ingredients of said medicaments, said mass ratio of triflusal to clopidogrel bisulfate is (250-650):(50-150).

4. The medicaments as recited in claim 1, wherein said mass ratio of triflusal to clopidogrel bisulfate is (285-315):(95-105).

5. The medicaments as recited in claim 1, wherein said mass ratio of triflusal to clopidogrel bisulfate is (570-630):(95-105).

6. The medicaments as recited in claim 1, wherein in said active ingredients of said medicaments, said mass ratio of triflusal to clopidogrel bisulfate is (1- 20):1.

7. The medicaments as recited in claim 1, wherein in said active ingredients of said medicaments, said mass ratio of triflusal to clopidogrel bisulfate is (300-600):98±5%, preferably 300:97.875 or 600:97.875.

8. The medicaments as recited in claim 1, wherein said medicaments of a unit therapeutic dose contain 130-800 mg said active ingredients.

9. The medicaments as recited in claim 8, wherein said medicaments of a unit therapeutic dose contain 100-600 mg triflusal and 30-100 mg clopidogrel bisulfate.

10. The medicaments as recited in claim 8, wherein said medicaments of a unit therapeutic dose contain 100-600 mg triflusal and 92-104 mg clopidogrel bisulfate, preferably 300-600 mg triflusal and 92-104 mg clopidogrel bisulfate.

11. The medicaments as recited in claim 8, wherein said medicaments of a unit therapeutic dose contain 285-315 mg triflusal and 95-105 mg clopidogrel bisulfate, preferably 300 mg triflusal and 100 mg clopidogrel bisulfate.

12. The medicaments as recited in claim 8, wherein said medicaments of a unit therapeutic dose contain 570-630 mg triflusal and 95-105 mg clopidogrel bisulfate, preferably 600 mg triflusal and 100 mg clopidogrel bisulfate.

13. The medicaments as recited in claim 9, wherein said medicaments are prepared for oral use as an oral application form selected from the group consisting of tablets, capsules, granules and dry suspension.

14. The medicaments as recited in claim 13, wherein said medicaments contain at least one of accessories as inactive ingredient which are selected from the group consisting of microcrystalline cellulose, sodium carboxymethyl starch, dextrin, lactose, and magnesium stearate.

15. The medicaments as recited in claim 14, wherein said medicaments are used in treatment of cardiovascular and cerebrovascular diseases, wherein said cardiovascular and cerebrovascular diseases are at least one of diseases selected from the group consisting of angina, coronary thrombus formation, and cerebral embolism.

16. The medicaments as recited in claim 1, wherein said medicaments are used to inhibit platelet aggregation.

17. The medicaments as recited in claim 1, wherein in said active ingredients of said medicaments, said mass ratio of triflusal to clopidogrel bisulfate is (100-600):(50-100).

18. The medicaments as recited in claim 1, wherein in said active ingredients of said medicaments, said mass ratio of triflusal to clopidogrel bisulfate is 3:1 or 6:1.

19. The medicaments as recited in claim 1, wherein said medicaments of a unit therapeutic dose contain 130-700 mg said active ingredients.

20. The medicaments as recited in claim 1, wherein said medicaments of a unit therapeutic dose contain 100-600 mg triflusal and 50-100 mg clopidogrel bisulfate and is capable of inhibiting platelet aggregation.

* * * * *